United States Patent
Pruitt et al.

(10) Patent No.: US 9,364,644 B2
(45) Date of Patent: Jun. 14, 2016

(54) INDEFLATOR FOR INFLATING THERAPEUTIC BALLOONS

(71) Applicant: Covidien LP, Mansfield, MA (US)

(72) Inventors: Sean Pruitt, Franklin, MA (US); Phillip Shaltis, Sharon, MA (US); Steven Cote, Mendon, MA (US)

(73) Assignee: Covidien LP, Mansfield, MA (US)

( * ) Notice: Subject to any disclaimer, the term of this patent is extended or adjusted under 35 U.S.C. 154(b) by 125 days.

(21) Appl. No.: 14/460,422

(22) Filed: Aug. 15, 2014

(65) Prior Publication Data

US 2016/0045718 A1    Feb. 18, 2016

(51) Int. Cl.
    *A61M 25/10*    (2013.01)

(52) U.S. Cl.
    CPC ................. *A61M 25/10182* (2013.11)

(58) Field of Classification Search
    CPC ............. A61M 25/10182; A61M 5/31526; A61M 5/31528; A61M 25/1018; A61M 5/31581; A61M 25/10184; A61M 25/10187; A61M 25/10181; A61M 5/315
    See application file for complete search history.

(56) References Cited

U.S. PATENT DOCUMENTS

| 4,832,692 | A | | 5/1989 | Box et al. |
| 4,994,065 | A | * | 2/1991 | Gibbs ................ A61B 17/8822 222/391 |
| 5,306,248 | A | | 4/1994 | Barrington |
| 5,752,935 | A | | 5/1998 | Robinson et al. |
| 2004/0122361 | A1 | | 6/2004 | Hart et al. |
| 2008/0077075 | A1 | | 3/2008 | Moreira et al. |

OTHER PUBLICATIONS

Medtronics, Everest Disposable Inflation Device and Accessories, at least as early as Aug. 14, 2014, 2 pages, Medtronic.com.

* cited by examiner

*Primary Examiner* — Bradley Osinski

(57) ABSTRACT

An indeflator for inflating a therapeutic balloon. A barrel has an interior chamber that receives fluid and an outlet in fluid communication with the interior chamber. A plunger sealingly engages the interior of the barrel. The plunger is selectively movable to dispense fluid through the outlet of the barrel. A coarse inflation control assembly includes a coarse inflation actuator that rotates about a coarse rotational axis to dispense fluid through the barrel at an inverse coarse inflation rate. A fine inflation control assembly includes a fine inflation actuator selectively rotatable about a fine rotational axis to dispense fluid through the outlet at an inverse fine inflation rate. The inverse fine inflation rate is greater than the inverse coarse inflation rate.

19 Claims, 10 Drawing Sheets

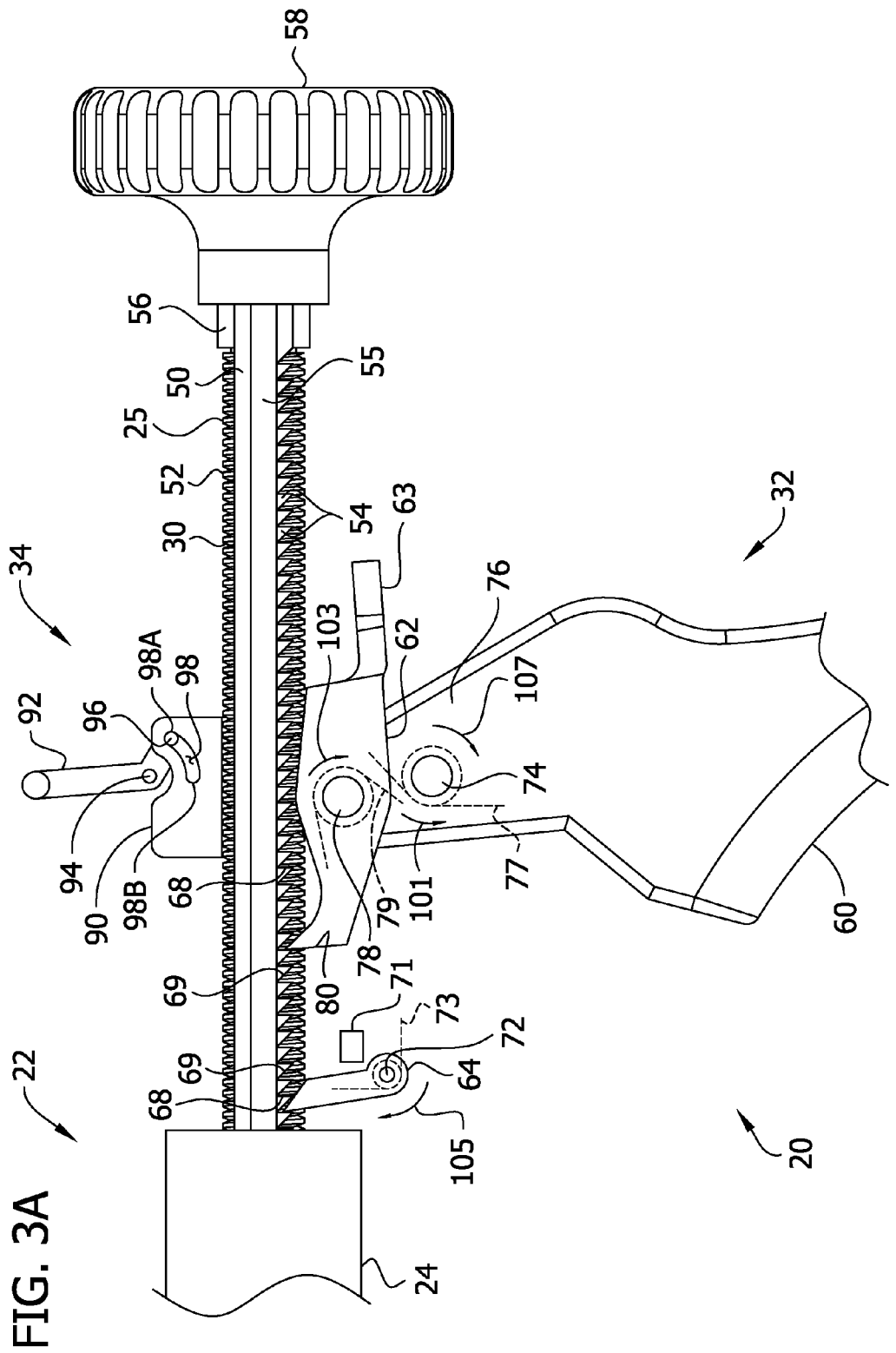

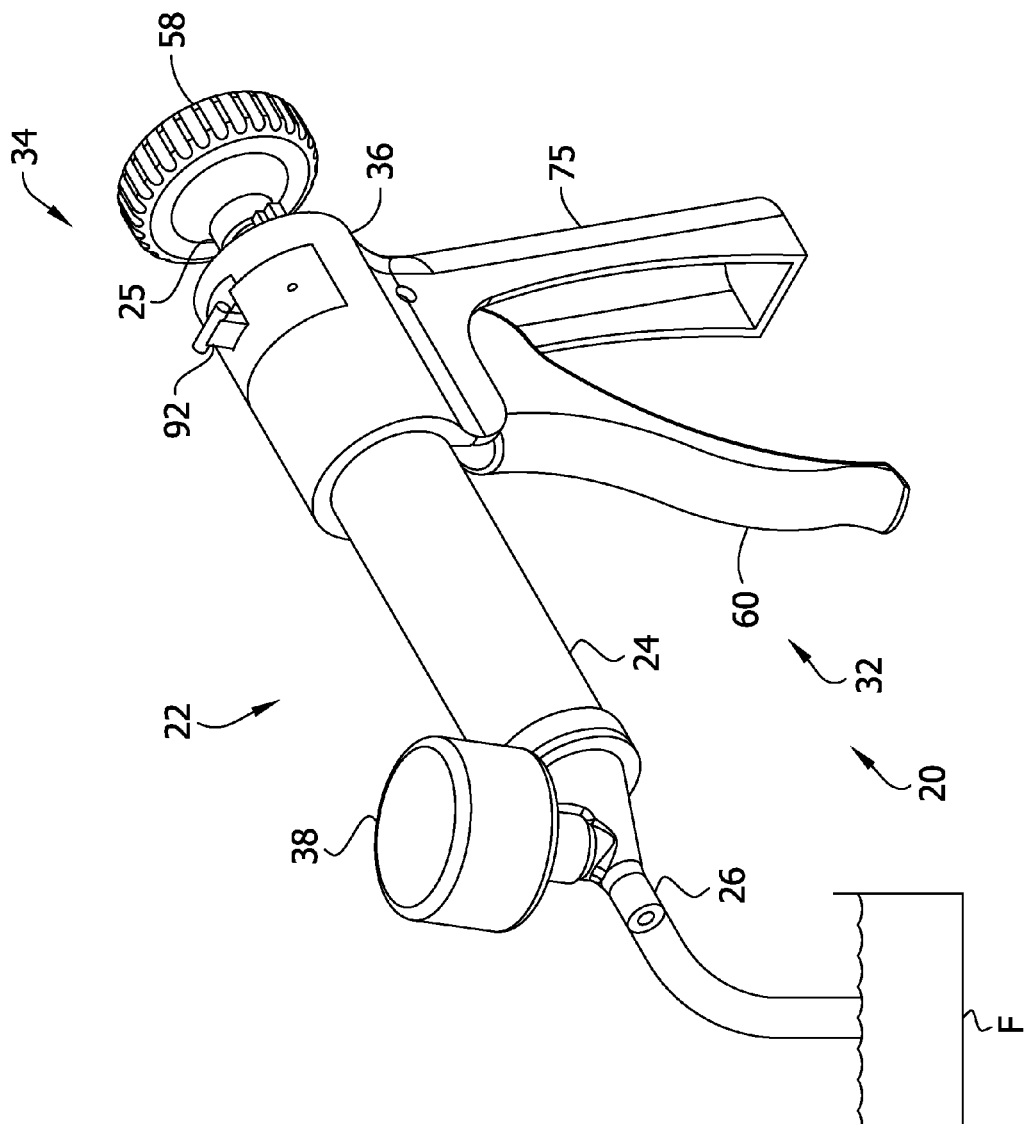

US 9,364,644 B2

INDEFLATOR FOR INFLATING THERAPEUTIC BALLOONS

BACKGROUND

The present invention generally relates to indeflators used to inflate therapeutic balloons.

Therapeutic balloons are used in a number of medical procedures including balloon angioplasty. An indeflator is commonly used to inflate therapeutic balloons to desired pressures. Often, the indeflator is a syringe-type device including a plunger that seals and engages a hollow interior of a barrel. The plunger may include a threaded rod or screw mated with an engagement member or nut. Rotation of the threaded rod relative to the nut translates the plunger within the barrel to dispense fluid (e.g., air or liquid) through a nozzle of the barrel and into the balloon. To inflate the balloons, medical practitioners manually twist the threaded plunger rod until enough fluid is dispensed into the balloon that it reaches its desired pressure and diameter. For large balloons, this can be a slow and physically demanding process.

SUMMARY

In an embodiment, the present invention includes an indeflator for inflating a therapeutic balloon. A barrel has an interior chamber that receives fluid and an outlet in fluid communication with the interior chamber. A plunger sealingly engages the interior of the barrel. The plunger is selectively movable to dispense fluid through the outlet of the barrel. A coarse inflation control assembly includes a coarse inflation actuator that rotates about a coarse rotational axis to dispense fluid through the barrel at an inverse coarse inflation rate. A fine inflation control assembly includes a fine inflation actuator selectively rotatable about a fine rotational axis to dispense fluid through the outlet at an inverse fine inflation rate. The inverse fine inflation rate is greater than the inverse coarse inflation rate.

In other embodiments, the invention includes an indeflator for inflating a therapeutic balloon of a balloon catheter using a ratcheting mechanism. The ratcheting mechanism is operatively connected to a plunger to impart linear movement of the plunger in an interior chamber of a barrel. The linear movement of the plunger dispenses fluid through a nozzle of the barrel.

Other aspects and embodiments will be apparent in view of the following description and claims.

BRIEF DESCRIPTION OF THE DRAWINGS

FIG. 3A is similar to FIG. 3 with a trigger actuator of the coarse inflation control assembly in a squeezed actuating position;

FIG. 5 is a perspective view of the indeflator in fluid communication with a fluid source, which is illustrated schematically;

Corresponding reference characters indicate corresponding parts throughout the drawings.

DETAILED DESCRIPTION

Figure 1:
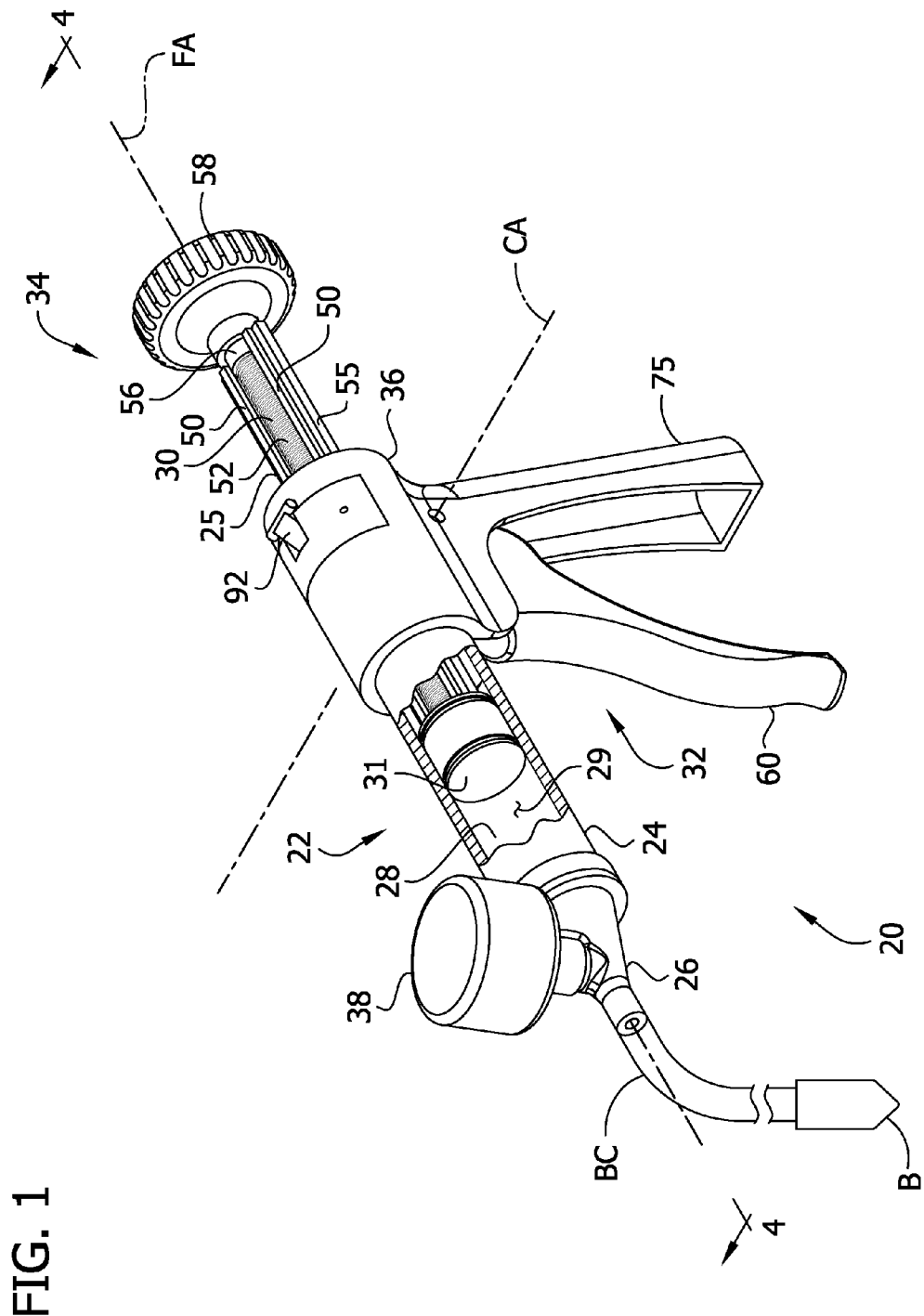
FIG. 1 is a perspective view of one embodiment of an indeflator and catheter with a portion of a barrel of the indeflator broken away to reveal a plunger received in the barrel and in fluid communication with a therapeutic balloon B, which is illustrated schematically.

Referring to FIG. 1, an embodiment of an indeflator for inflating therapeutic balloons of balloon catheters is designated in its entirety by reference number 20. The indeflator 20 comprises syringe assembly 22, including a barrel 24 and a plunger 25 received in the barrel. A nozzle 26 defining an open distal longitudinal end of the barrel 24 is removably connected to a proximal end of a balloon catheter BC and is in fluid communication with a therapeutic balloon B of the balloon catheter for inflating the balloon. The balloon B is illustrated schematically in an inflated state. The barrel 24 is generally elongate having an interior surface 28 defining an interior chamber 29 for receiving and holding fluid therein. The plunger 25 includes an elongate plunger body, generally indicated at reference numeral 30, and a plunger head 31 secured to a distal end of the plunger body. The plunger head 31 sealingly engages the interior surface 28 of the barrel 24 and is slidable within the interior chamber 29 to dispense fluid through the nozzle 26 as the plunger 25 moves distally in the interior chamber, as explained in more detail below. A pressure gauge 38 is in fluid communication with the nozzle 26 to measure the internal pressure in the therapeutic balloon B.

Referring still to FIG. 1, the indeflator 20 further includes a coarse inflation control assembly, generally indicated at 32, and a fine inflation control assembly, generally indicated at 34. As will be discussed in more detail below, the coarse inflation control assembly 32 allows a user to quickly deliver a relatively large volume of fluid for inflating a relatively large balloon (i.e., a balloon with a relatively large interior inflation volume), and the fine inflation control assembly 34 allows a user to more accurately deliver a relatively small volume for inflating a relatively small balloon (i.e., a balloon with a relatively small interior inflation volume) or adding a relatively small volume of fluid to a large volume balloon that is partially inflated. In the illustrated embodiment, the coarse and fine inflation control assemblies 32, 34, respectively, are at least partially housed in an inflation control housing 36.

In the illustrated embodiment, the coarse inflation control assembly 32 includes a trigger or coarse inflation actuator 60 selectively rotatable about a coarse rotational axis CA to impart linear movement of the plunger 25 in the interior chamber 29 of the barrel 24 for dispensing fluid through the outlet of the barrel (e.g., the nozzle 26). The coarse inflation control assembly 32 has an inverse coarse inflation rate defined as a ratio of angular displacement (degrees) of the coarse inflation actuator 60 about the coarse rotational axis CA to linear displacement (mm) of the plunger 25 in the interior chamber imparted by the angular displacement of the coarse inflation actuator. In one example, the inverse coarse inflation rate may be from about 4.5 degrees/mm to about 7.5 degrees/mm. As will be discussed in greater detail below, in the illustrated embodiment, the coarse inflation control assembly 32 is a ratcheting mechanism, and the coarse inflation control actuator 60 is a trigger. However, it is contemplated that other mechanisms for the coarse inflation control assembly may also be used to produce the inverse coarse inflation rate without departing from the scope of the invention. In one embodiment, the indeflator 20 may include the coarse inflation control assembly 32 (e.g., the ratcheting mechanism) and the fine inflation control assembly 34 may be omitted.

In the illustrated embodiment, the fine inflation control assembly 34 includes a fine inflation actuator 58 selectively rotatable about a fine rotational axis FA to impart linear movement of the plunger 25 in the interior chamber 29 of the barrel 24 for dispensing fluid through the outlet of the barrel (e.g., the nozzle 26). The fine inflation control assembly 34 has an inverse fine inflation rate defined as a ratio of angular displacement (degrees) of the fine inflation actuator 58 about the fine rotational axis FA to linear displacement (mm) of the plunger 25 in the interior chamber 29 imparted by the angular displacement of the fine inflation actuator. In one example, the inverse fine inflation rate may be from about 1800 degrees/mm to about 360 degrees/mm. The inverse fine inflation rate is greater than the inverse coarse inflation rate, such that angular displacement of the coarse inflation actuator 60 imparts a greater linear displacement of the plunger 25 than the same angular displacement of the fine inflation actuator 58. For example, the ratio of the inverse fine inflation rate to the coarse inflation rate may be from about 10:1 to about 20:1. As will be discussed in greater detail below, in the illustrated embodiment, the fine inflation control assembly 34 is a screw mechanism (e.g., a leadscrew mechanism), and the fine inflation control actuator 58 is a rotatable knob. However, it is contemplated that other mechanisms for the fine inflation control assembly may also be used to produce the inverse fine inflation rate without departing from the scope of the invention.

Figure 2:
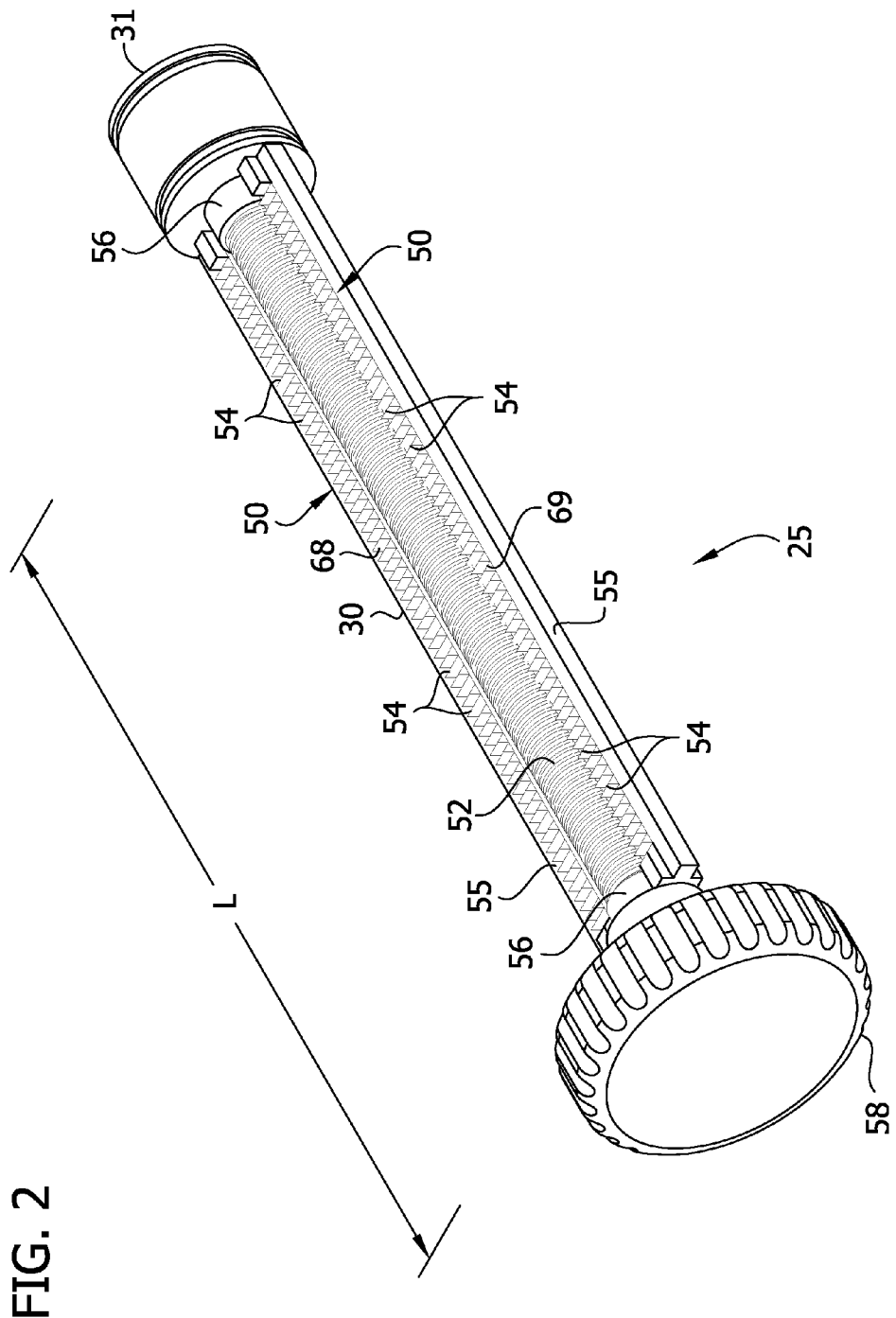
FIG. 2 is a bottom perspective view of the plunger of the indeflator.

Referring to FIG. 2, in the illustrated embodiment, the plunger body 30 includes a pair of ratchet bars 50 and a threaded rod 52. The ratchet bars 50 are disposed diametrically on either side of the threaded rod 52. Each ratchet bar 50 has a length L and a plurality of teeth 54 spaced apart along its length. Each ratchet bar 50 has a laterally extending projection 55 (e.g., a tongue) slidably received in a track (e.g., a groove) defined by the control housing 36 or another portion of the indeflator 20 to allow distal and proximal translation of the ratchet bars while inhibiting rotation of the ratchet bars about their longitudinal axes. The threaded rod 52 includes one or more external helical threads extending lengthwise of the rod. In the illustrated embodiment, the threaded rod 52 is rotatably coupled to proximal and distal bearing collars 56 connected to opposite longitudinal ends of the ratchet bars 50. The collars 56 receive respective portions of the threaded rod 52 therein such that the threaded rod is free to rotate in the collars about its longitudinal axis. The threaded rod 52 translates conjointly with the ratchet bars 50 such that distal and proximal movement of either the ratchet bars or the threaded rod imparts corresponding movement to the other. The proximal end of the threaded rod 52 extends through the proximal collar 56 and is secured to the knob 58 (i.e., the fine inflation actuator). The knob 58 may be used to rotate the threaded rod 52 about its longitudinal axis in the bearing collars 56.

Figure 3:
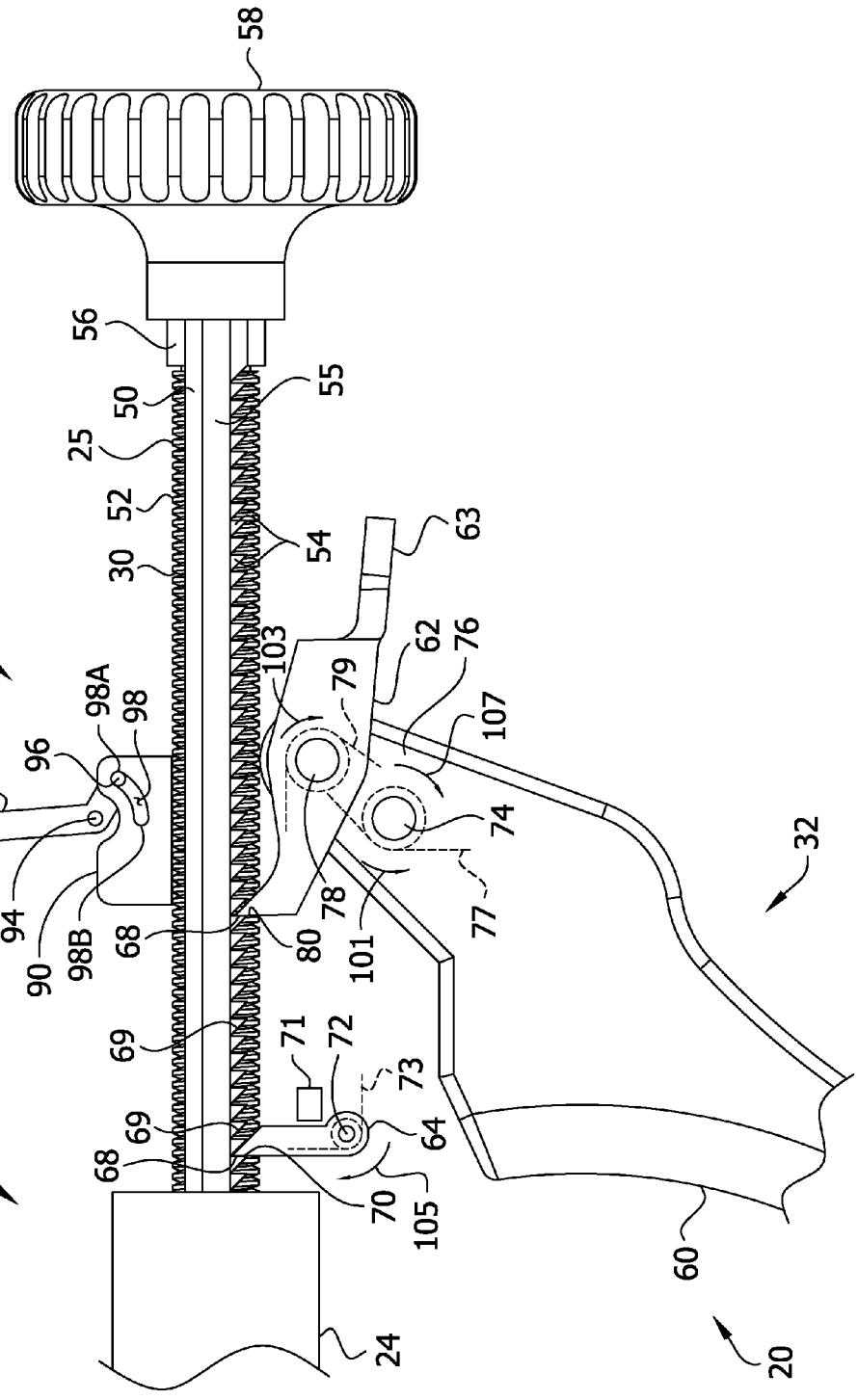
FIG. 3 is an enlarged fragmentary side elevational view of the indeflator with an inflation control housing removed.

As shown in FIG. 3, in the illustrated embodiment, the coarse inflation control assembly 32 comprises a ratcheting mechanism. Although, it should be understood that other mechanisms for the coarse inflation control assembly may also be used without departing from the scope of the invention. The ratcheting mechanism 32 includes the pair of ratchet bars 50, the trigger 60 (broadly, an actuator), a driving pawl 62, and a holding pawl 64. In the illustrated embodiment, the ratchet bars 50 are shared components of the ratcheting mechanism 32 and the plunger 25. Although not shown in FIG. 3, a second driving pawl and a second holding pawl may be respectively linked to the illustrated driving pawl 62 and holding pawl 64 to engage with the opposite ratchet bar 50 in the same way that the illustrated driving pawl and holding pawl engage with the illustrated ratchet bar. Still other components may also be used without departing from the scope of the invention.

Referring to FIGS. 3 and 3A, in the illustrated embodiment, the trigger 60 actuates distal translation (e.g., linear movement) of the plunger 25 in the interior chamber 29 of the barrel 24 to expel fluid in the barrel through the nozzle 26 and into the balloon B. The trigger 60 is rotatably secured to a pin 74. When the trigger 60 is actuated (e.g., by being squeezed toward a handle portion 75 of the inflation control housing 36 (FIG. 1)), it rotates in an actuating direction 101 about the pin 74. As the trigger 60 rotates in the actuating direction 101, a lever portion 76 of the trigger 60 moves generally in the distal direction. The driving pawl 62 is rotatably secured to the lever portion 76 at a pin 78 and is biased in an engagement direction 103 using, for example, a torsion spring 79, to bias the driving pawl in an engagement position in which a leading end 80 of the driving pawl engages trailing end 68 of a ratchet tooth 54. When the trigger 60 is actuated (e.g., rotated about the pin 74), as shown in FIG. 3A, the lever portion 76 advances the driving pawl 62 in the distal direction and the torsion spring 79 maintains the driving pawl in its engagement position, thereby imparting translation (e.g., linear movement) of the plunger 25 in the distal direction within the barrel 24. As the plunger 25 translates distally, the holding pawl 64 rotates against a bias force (e.g., a torsion spring 73) around a pin 72 (anchored, for example, in the inflation control housing 36) to allow the sloped leading ends 69 of the teeth 54 to slide distally past the leading end 70 of the holding pawl, after which, the leading end of the holding pawl 64 returns under the bias force to engage a respective trailing end 68 of another ratchet tooth 54. The illustrated torsion spring 73 applies a bias force on the locking direction 105. To prevent over-rotation of the holding pawl 64 in the locking direction 105, a locking structure 71 is positioned adjacent the holding pawl in use. Engagement between the locking structure 71 and the holding pawl 64 prevents the holding pawl from over-rotating, and engagement between the leading end 70 of the holding pawl and the trailing end 68 of a ratchet tooth 54 prevents the plunger 25 from sliding proximally in the interior chamber 29 of the barrel 24 in response to back pressure as the therapeutic balloon B is expanded.

Referring to FIG. 3, the trigger 60 is biased in the non-actuating direction 107, for example, using a torsion spring 77, such that the trigger automatically returns to a relaxed, initial position once it is released. As the trigger 60 returns to the initial position, the lever portion 76 moves in the proximal direction, carrying the driving pawl 62 with it. As the driving pawl 62 moves in the proximal direction, it slides over sloped leading ends 69 of the teeth 54 and rotates in a direction opposite the engagement direction 103, against the bias of the torsion spring 79. Because the driving pawl 62 is biased in the engagement direction 103, it engages a different ratchet tooth 54 (e.g., the leading end 80 of the driving pawl engages the trailing end 68 of the different ratchet tooth) once the trigger 60 returns to the initial position (e.g., once the leading end of the driving pawl moves proximally past the trailing end of the different ratchet tooth). When the trigger 60 is in the initial position, the driving pawl 62 is biased in its engagement position and acts as a stop inhibiting proximal movement of the plunger 25 in the barrel 24. Together, the holding pawl 64 and the driving pawl 62 prevent the plunger 25 from sliding proximally in the interior chamber 29 of the barrel 24. As will be discussed in greater detail below, it is, at times, helpful to slide the plunger 25 in the interior chamber 29 of the barrel 24 to draw fluid into the barrel. To disengage the driving pawl 62, an upward force (i.e., upward with respect to the view of FIGS. 3-3A) may be applied to a disengagement tab 63 to rotate the driving pawl against the bias force of the torsion spring 79 in a direction opposite the engagement direction 103 to a disengaged position in which the leading end 80 of the driving pawl does not engage a ratchet tooth 54. To disengage the holding pawl 64, the locking structure 71 is moved away from the holding pawl to allow the holding pawl to continue rotating in the locking direction 105 past an engaged position with respect to the ratchet teeth 54 in response to the biasing force of the torsion spring 73. When neither the holding pawl 64 nor the driving pawl 62 is engaged with the ratchet teeth 54, the ratcheting mechanism 32 is in the disengaged position.

Figure 4:
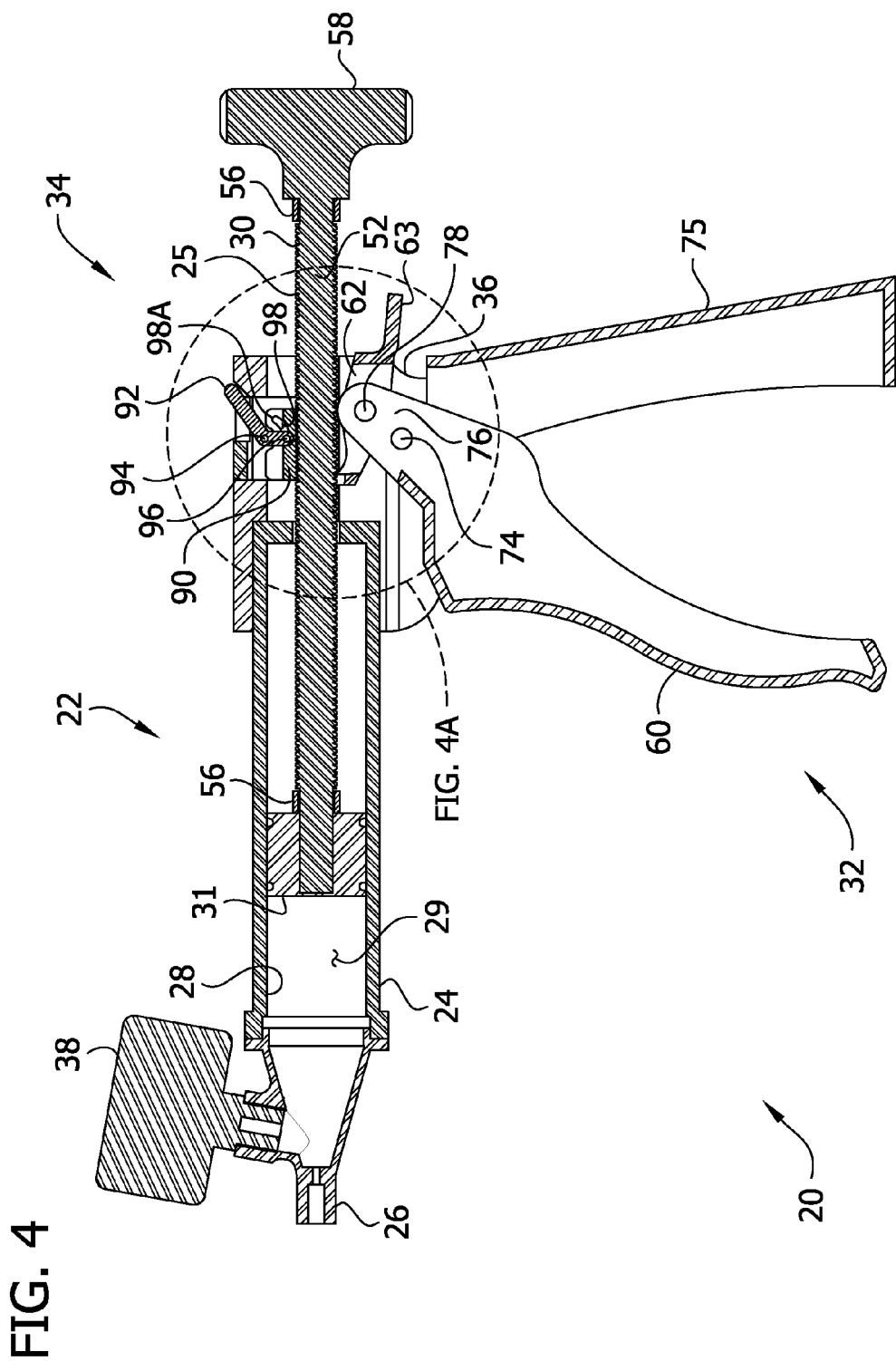
FIG. 4 is a longitudinal section view of the indeflator taken along the line 4-4 in FIG. 1.
Figure 4A:
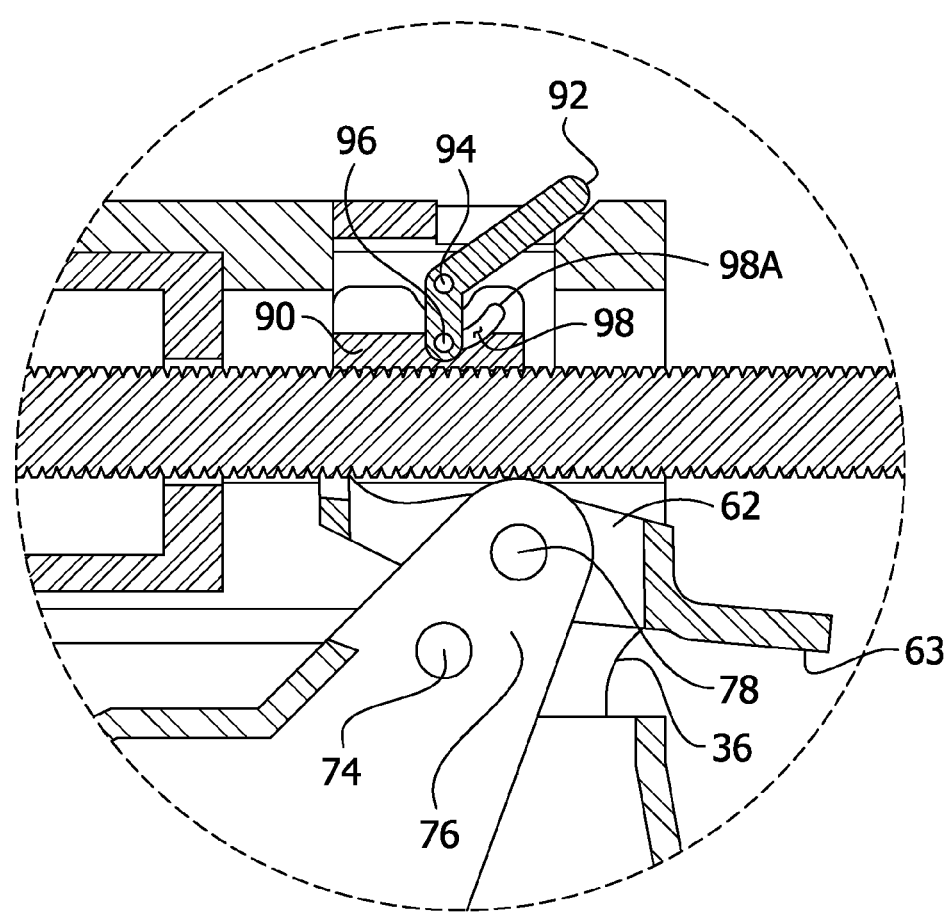
FIG. 4A is an enlarged, partial view of FIG. 4.

As shown in FIG. 4, the fine inflation control assembly 34 of the illustrated embodiment comprises a screw mechanism (e.g., a leadscrew mechanism). The fine inflation control assembly 34 may comprise a different mechanism without departing from the scope of the invention. The threaded rod 52 of the illustrated embodiment is a shared component between the screw mechanism 34 and the plunger 25. A leadscrew nut 90 (e.g., an open nut (as shown), a closed nut, or a split nut; broadly, an engagement member) is configured to selectively engage the helical thread of the threaded rod 52 such that, when in an engaged position as shown in FIGS. 4 and 4A, the threaded rod (or screw) translates through its rotation relative to the engagement member (or leadscrew nut). Thus, when the threaded rod 52 is rotated in an inflating direction (e.g., clockwise direction) using the knob 58, the plunger 25 slides distally in the interior chamber 29 of the barrel 24. When the threaded rod 52 is rotated in a deflating direction (e.g., counterclockwise direction), the plunger 25 slides proximally in the interior chamber 29 of the barrel 24. As discussed in more detail below, the screw mechanism 34 may be used to slide the plunger 25 in the interior chamber 29 of the barrel 24 in the distal or proximal direction in very small increments to precisely control the pressure of the fluid in a small-volume therapeutic balloon B or partially filled large-volume therapeutic balloon.

Figure 4B:
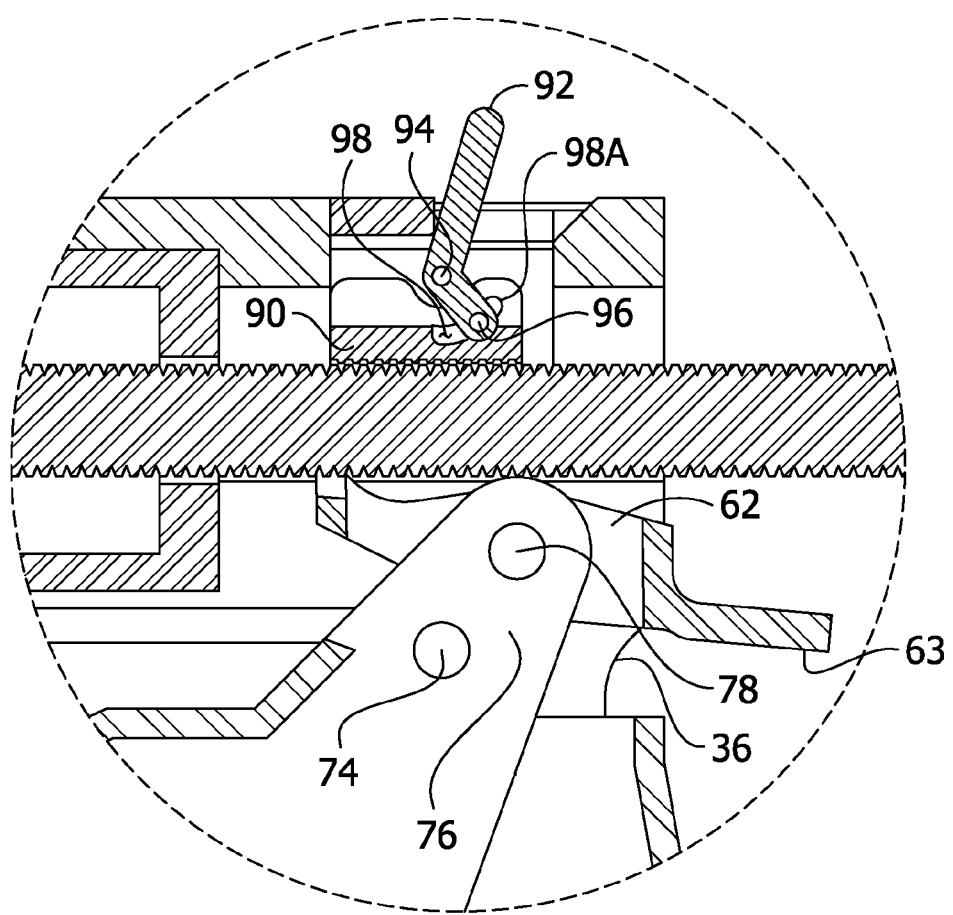
FIG. 4B is similar to FIG. 4A with an engagement member of a fine inflation control assembly in a disengaged position.

As shown in FIGS. 4A and 4B, in the illustrated embodiment, the engagement member 90 may be selectively engaged with and disengaged from the threaded rod 52. A lever 92 is rotatably attached to the inflation control housing 36 with a pin 94. A cam member 96 projects laterally outward from the lever 92 and is received in a slot 98 of the engagement member 90. The engagement member 90 acts as a follower to motion of the cam member 96 in a radial direction with respect to the axis of rotation FA of the threaded rod. The lever 92 is rotated about the pin 94, which in turn causes movement of the cam member 96. When the cam member 96 is configured in a disengaged position (with the cam member having been rotated toward the disengaged end 98A of the slot 98 (FIG. 4B)), the engagement member 90 is lifted away from operative engagement with the threaded rod 52. When the cam member 96 is configured in the engaged position (with the cam member positioned adjacent the engaged end 98B of the slot 98 (FIG. 4A)), the engagement member 90 is held (e.g., with a force applied by the cam member 96 against the slot 98) in operative engagement with the threaded rod 52. As will be explained in more detail below, when the engagement member 90 is in the disengaged position, the ratcheting mechanism 32 may be used to slide the plunger 25 distally in the interior chamber 29 of the barrel 24. When the engagement member 90 is in the engaged position, the engagement between the engagement member and the threaded rod 52 prevents the ratcheting mechanism 32 from sliding the plunger 25 distally in the interior chamber 29 of the barrel 24.

Referring to FIG. 5, the indeflator 20 is shown in an empty state, such as may be common prior to use of the indeflator in a therapeutic procedure. In order to draw fluid from a fluid source F into the interior chamber 29 of the barrel 24, the screw mechanism 34 and the ratcheting mechanism 32 must each be configured in a disengaged position. As discussed above, to disengage the driving pawl 62, a force may be applied to a disengagement tab 63 (FIG. 3) to rotate the driving pawl against the bias force of the torsion spring 79 in a direction opposite the engagement direction 103 to a disengaged position in which the driving pawl does not engage a ratchet tooth 54. To disengage the holding pawl 64, the locking structure 71 is moved away from the holding pawl to allow the holding pawl to continue rotating in the locking direction 105 (e.g., due to the bias force of the torsion spring 73) past an engaged position with respect to the ratchet teeth 54. To disengage the screw mechanism 34, the lever 92 is positioned to rotate the cam member 96 toward its disengaged position (e.g., the cam member is rotated toward the disengaged end 98A of the slot 98 (FIG. 4A)). Once the ratcheting mechanism 32 and the screw mechanism 34 have been positioned in respective disengaged positions, wherein the mechanisms that prevent the plunger 25 from sliding proximally in the interior chamber 29 of the barrel 24 are disengaged, a manually applied sliding force will easily slide the plunger in the proximal direction. For example, a user may apply a proximal axial force to the knob 58 to draw the plunger 25 proximally of the barrel 24. In FIG. 5, the nozzle 26 has been fluidly connected to a fluid source F. Drawing the plunger 25 proximally of the barrel 24 will draw fluid from the fluid source F into the interior chamber 29 of the barrel. Suitable fluid sources may include saline or other fluids, including liquids and gases.

Figure 6:
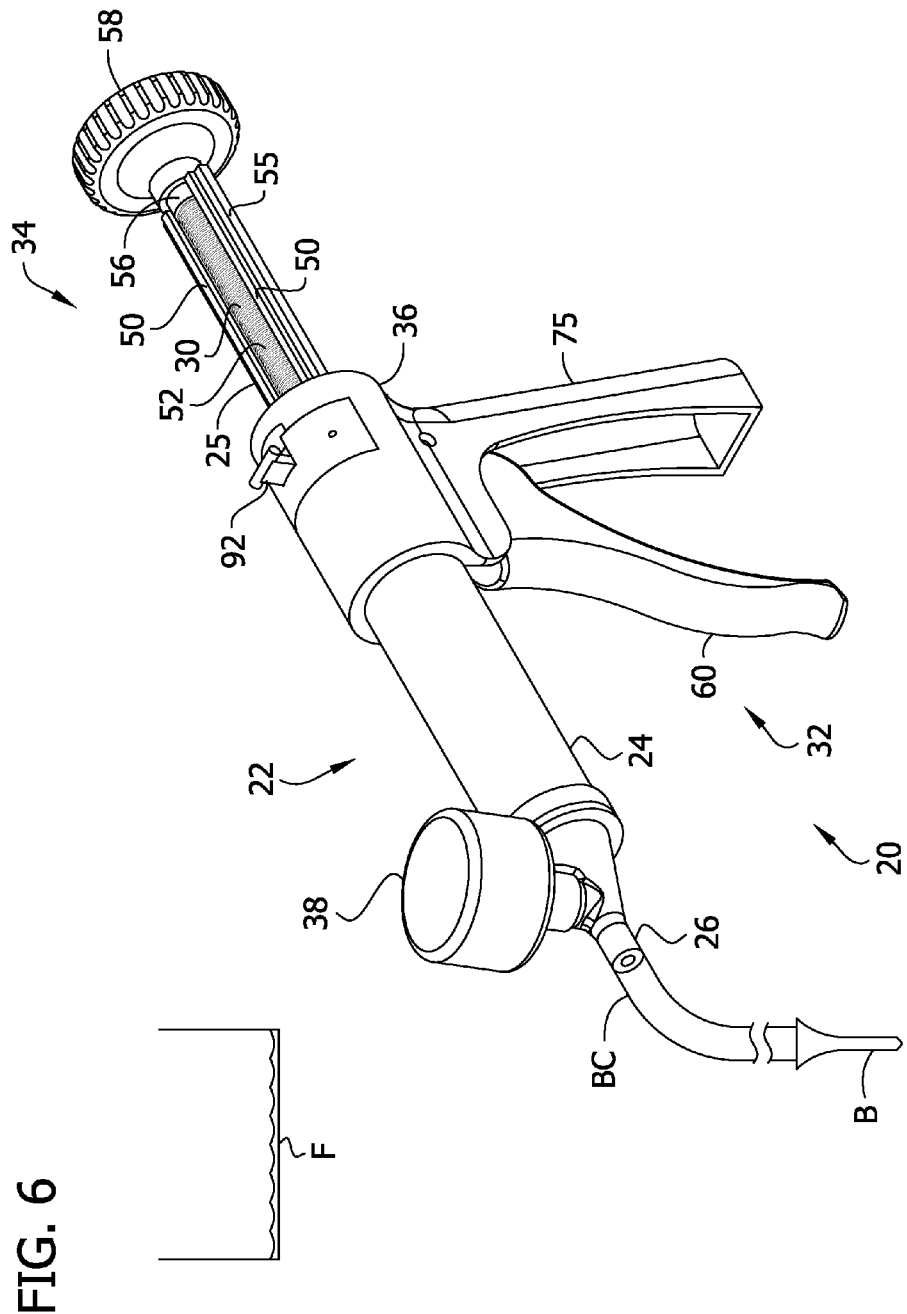
FIG. 6 is a perspective view of the indeflator and catheter in fluid communication with an empty therapeutic balloon, which is illustrated schematically.

In FIG. 6, the indeflator 20 is shown in filled state. The plunger 25 has been pulled back proximally of the barrel 24, which has drawn in fluid from the fluid source F. The indeflator 20 is now filled with the fluid. The nozzle 26 is fluidly disconnected from the fluid source F and connected to the balloon catheter BC such that the indeflator is in fluid communication with an empty therapeutic balloon B of the balloon catheter. The therapeutic balloon B may be suitable for use in balloon angioplasty or other balloon therapies. These therapies are well-understood by those skilled in the art and will not be discussed in further detail here. From this filled state, a user may choose whether to inflate the therapeutic balloon B using the ratcheting mechanism 32 or the screw mechanism 34. In some embodiments, the ratcheting mechanism 32 is used to inflate large-volume therapeutic balloons B and the screw mechanism 34 is used to inflate small-volume therapeutic balloons.

In one example, assuming the illustrated therapeutic balloon B is a large-volume balloon, the ratcheting mechanism 32 is first reconfigured from the disengaged position to an engaged position. For example, to engage the driving pawl 62, a force (e.g., a passive force applied by the torsion spring 79) may be applied to a disengagement tab 63 to rotate the driving pawl in the same direction as the bias force of the torsion spring 79 (i.e., the engagement direction 103). To engage the holding pawl 64, the locking structure 71 is moved toward the holding pawl to rotate the holding pawl against the bias force of the torsion spring 73 and opposite the locking direction 105 to an engaged position with respect to the ratchet teeth 54. In the engaged position, a leading end 70 of the holding pawl 64 engages a trailing end 68 of a ratchet tooth 54 to prevent the plunger 25 from sliding proximally in the interior chamber 29 of the barrel 24. As discussed above, to enable the ratcheting mechanism 32, the screw mechanism 34, and more specifically the engagement member 90, should be configured in a disengaged position. The ratcheting mechanism 32 is enabled such that squeezing the trigger 60 (i.e., rotating the coarse inflation control actuator about the coarse inflation control axis CA (FIG. 1)) toward the handle portion 75 of the inflation control housing 36 will slide the plunger 25 distally in the interior chamber 29 of the barrel 24. The leading end 80 of the driving pawl 62 is engaged with a trailing end 68 of a ratchet tooth 54 to apply a force to the ratchet bar 50 in the distal direction. The distal force slides the plunger 25 distally in the interior chamber 29 of the barrel 24. As the plunger 25 slides distally in the interior chamber 29 of the barrel 24, fluid is dispensed through the nozzle 26 to create a positive pressure in the therapeutic balloon B. The trigger 60 is released, and the ratcheting mechanism 32 is returned to a relaxed position. As discussed above, the leading end 70 of the holding pawl 64 engages a trailing end 68 of a ratchet tooth 54 to prevent the plunger 25 from sliding proximally in the interior chamber 29 of the barrel 24 as the ratcheting mechanism 32 returns to the relaxed position. Once in the relaxed position, the ratcheting mechanism 32 prevents the plunger 25 from sliding proximally in the interior chamber 29 of the barrel 24. The steps of squeezing and releasing the trigger 60 may be repeated until the therapeutic balloon B reaches the desired inflated state (FIG. 1).

In another example, assuming the illustrated therapeutic balloon B is a small-volume balloon, the screw mechanism 34 is used instead of the ratcheting mechanism 32. Using the screw mechanism 34 from the filled state, the lever 92 is moved to an engaged position in which the cam member 96 engaged an engaged end 98B of the slot 98 securing the engagement member 90 in operative engagement with the threaded rod 52. When the engagement member 90 is in the engaged position, the screw mechanism 34 is enabled. In the illustrated embodiment, the knob 58 may be rotated (i.e., the fine inflation control actuator is rotated about the fine inflation control axis FA) in the inflating direction to dispense fluid into the therapeutic balloon B. The engagement member 90 engages the helical thread of the threaded rod 52. As the threaded rod 52 rotates about its longitudinal axis, it translates through its rotation relative the engagement member 90. The knob 58 is rotated until the therapeutic balloon B reaches the desired inflated state (FIG. 1). Use of the screw mechanism 34 does not require the ratcheting mechanism 32 be configured in the disengaged position, although it may be disengaged. As the plunger 25 slides distally in the interior chamber 29 of the barrel 24, the sloped leading ends 69 of the ratchet teeth 54 will push the holding pawl 64 and the driving pawl 62 against their respective biasing forces until a trailing end 68 of the ratchet tooth passes distally over respective leading ends 70 and 80 of the pawls.

It should be understood that the screw mechanism 34 may be used as the only inflation mechanism for inflating small-volume therapeutic balloons B. It should also be understood that the ratcheting mechanism 32 may be used as the only inflation mechanism for inflating large-volume therapeutic balloons B. However, in some instances, it may be desirable to inflate a large-volume therapeutic balloon B to a precise desired pressure. In these embodiments, the ratcheting mechanism 32 and the screw mechanism 34 may be used in combination to achieve the desired result. It is also contemplated that other coarse inflation control assemblies and fine inflation control assemblies may be used to carry out the steps of the method of inflating a therapeutic balloon B discussed below without departing from the scope of the invention.

Figure 7:
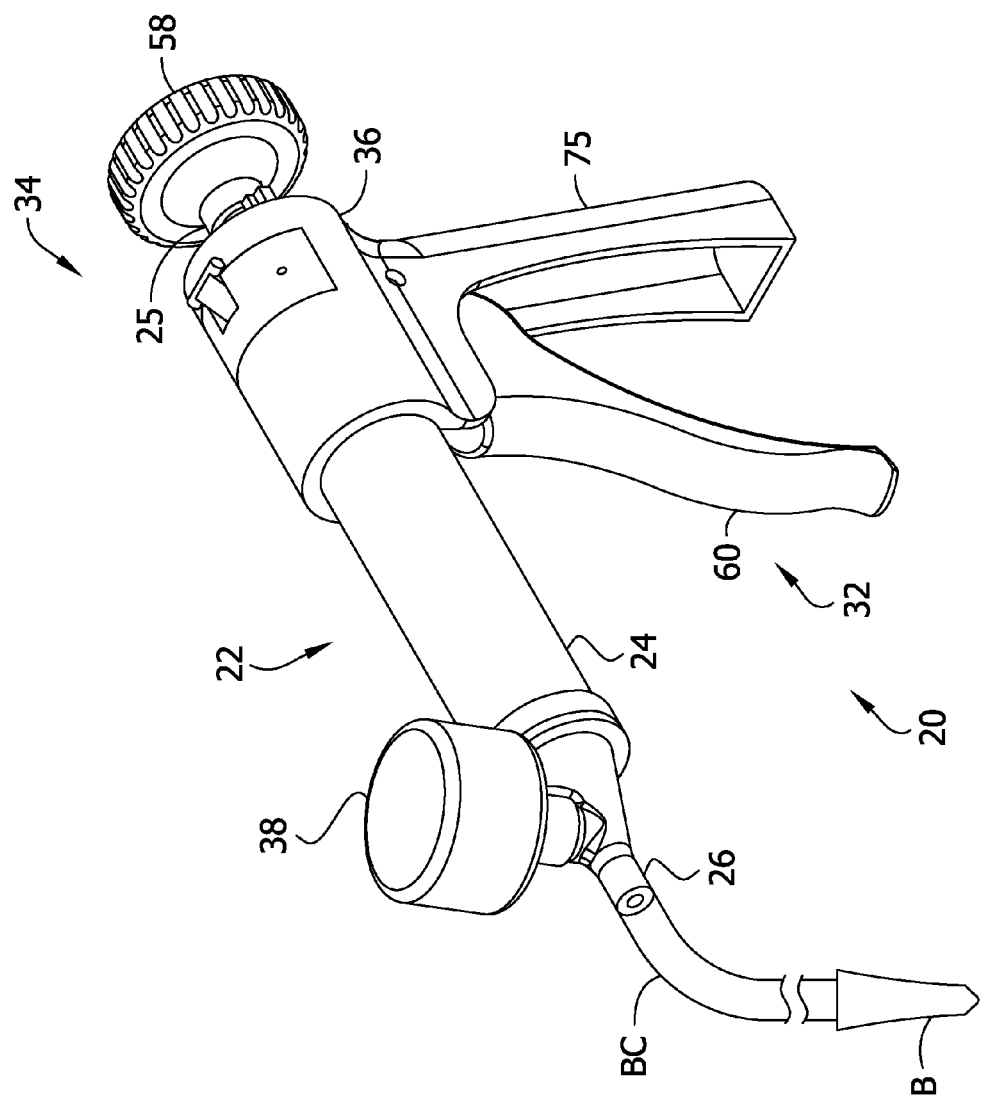
FIG. 7 is similar to FIG. 6.

For example, the ratcheting mechanism 32 is actuated to inflate the therapeutic balloon B from an empty state, as shown schematically in FIG. 6, to a coarsely inflated state (e.g., a state in which the balloon B is near the desired pressure), as shown schematically in FIG. 7. As discussed above, the balloon B may be inflated to the coarsely inflated state by alternatingly squeezing the trigger 60 toward the handle portion 75 and releasing the trigger. The steps of squeezing and releasing the trigger 60 may be repeated until the therapeutic balloon B reaches the coarsely inflated state. It should be noted that the step of squeezing the trigger 60 may be performed without squeezing the trigger all the way against the handle portion 75 of the inflation control housing 36. As discussed above, the holding pawl 64 sequentially engages each of the ratchet teeth 54 as the plunger 25 slides distally in the interior chamber 29 of the barrel 24. Thus, the trigger 60 may be squeezed to an intermediate position in which the holding pawl 64 engages a suitable one of the ratchet teeth 54 to inflate the balloon B to a suitable pressure (in this case, the coarsely inflated state). In some embodiments, the coarsely inflated state may have a pressure that deviates up to about ±5% from the desired pressure. The user may, for example, use pressure readings supplied by the pressure gauge 38 to determine when the balloon B has reached the coarsely inflated state.

Once the therapeutic balloon B has reached the coarsely inflated state, the engagement member 90 of the fine inflation control assembly 34 (e.g., the screw mechanism) may be switched from the disengaged position to the engaged position, as illustrated in FIG. 7. When the engagement member 90 is in the engaged position, the screw mechanism 34 is enabled. Thus, to inflate the therapeutic balloon B to a finely inflated state in which it is at a desired pressure, the screw mechanism 34 is actuated. As discussed above, the knob 58 may be rotated in the inflating direction to increase the pressure in the balloon B if the coarsely inflated state is at a pressure less than the desired pressure. Likewise, if fluid in the coarsely inflated balloon B has a pressure greater than the desired pressure, the knob 58 may be rotated in the deflating direction. If the knob 58 is rotated in the deflating direction, the threaded rod 52 translates in the proximal direction and slides the plunger 25 proximally in the interior chamber 29 of the barrel 24 to decrease the pressure in the therapeutic balloon B. The knob 58 may be rotated until the therapeutic balloon B reaches the finely inflated state and the desired pressure. The user may, for example, use pressure readings supplied by the pressure gauge 38 to determine when the balloon B has reached the finely inflated state.

Because the threaded rod 52 of the illustrated embodiment has a continuous helical thread path, the user can achieve inflation accuracy in the finely inflated state. In the illustrated embodiment, the user may consider the pressure readings from the pressure gauge 38 to recognize when the therapeutic balloon B has reached a suitable pressure, including the respective coarsely and finely inflated states. In combination, the ratcheting mechanism 32 and the screw mechanism 34 inflate a large-volume therapeutic balloon B to a desired pressure. Though the preceding discussion provides a sequence of steps for using the indeflator 20, one skilled in the art would appreciate that various steps or sequences of steps described above may be repeated, omitted, or rearranged without departing from the scope of the invention.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. An indeflator for inflating a therapeutic balloon to a desired pressure comprising:
   a barrel having an interior surface defining an interior chamber configured to receive fluid, and an outlet in fluid communication with the interior chamber;
   a plunger sealingly engaging the interior surface of the barrel, wherein the plunger is selectively movable linearly within the interior chamber for dispensing fluid through the outlet of the barrel;
   a coarse inflation control assembly including a coarse inflation actuator selectively rotatable about a coarse rotational axis to impart linear movement of the plunger in the interior chamber for dispensing fluid through the outlet of the barrel, wherein the coarse inflation control assembly has an inverse coarse inflation rate defined as a ratio of angular displacement (degrees) of the coarse inflation actuator about the coarse rotational axis to linear displacement (mm) of the plunger in the interior chamber imparted by the angular displacement of the coarse inflation actuator; and
   a fine inflation control assembly including a fine inflation actuator selectively rotatable about a fine rotational axis to impart linear movement of the plunger in the interior chamber for dispensing fluid through the outlet of the barrel, wherein the fine inflation control assembly has an inverse fine inflation rate defined as a ratio of angular displacement (degrees) of the fine inflation actuator about the fine rotational axis to linear displacement (mm) of the plunger in the interior chamber imparted by the angular displacement of the fine inflation actuator,
   wherein the inverse fine inflation rate is greater than the inverse coarse inflation rate.

2. The indeflator of claim 1, wherein the coarse inflation control assembly comprises a ratcheting mechanism.

3. The indeflator of claim 2, wherein the ratcheting mechanism comprises a ratchet bar having a length and a plurality of teeth spaced apart along its length.

4. The indeflator of claim 3, wherein the ratchet bar is operatively connected to the plunger.

5. The indeflator of claim 3, wherein the ratcheting mechanism comprises a driving pawl biased toward operative engagement with one of the teeth of the ratchet bar.

6. The indeflator of claim 5, wherein the coarse inflation actuator comprises a trigger operatively connected to the driving pawl to selectively advance the driving pawl and impart linear movement of the plunger in the interior chamber of the barrel.

7. The indeflator of claim 6, further comprising a holding pawl configured to sequentially engage the teeth of the ratchet bar as the plunger moves linearly in the interior chamber of the barrel.

8. The indeflator of claim 1, wherein the fine inflation control assembly comprises a screw mechanism.

9. The indeflator of claim 8, wherein the screw mechanism comprises a threaded rod.

10. The indeflator of claim 9, wherein the threaded rod is operatively connected to the plunger.

11. The indeflator of claim 10, wherein the screw mechanism comprises an engagement member configured to selectively, threadably mate with threaded rod to convert rotational motion of the threaded rod to linear motion to thereby impart linear movement of the plunger in the interior chamber of the barrel.

12. An indeflator for inflating a therapeutic balloon of a balloon catheter, the indeflator comprising:
    a barrel having a length, an interior surface defining an interior chamber extending along the length of the barrel and configured to receive a fluid, and a nozzle in fluid communication with the interior chamber and configured to operatively connect to the balloon catheter for fluidly connecting the barrel to the therapeutic balloon;
    a plunger sealingly engaging the interior surface of the barrel, wherein the plunger is selectively slidable linearly within the interior chamber to dispense fluid through the nozzle of the barrel;
    a ratcheting mechanism operatively connected to the plunger to selectively impart linear movement of the plunger in the interior chamber to dispense fluid through the nozzle;
    a screw mechanism operatively connected to the plunger to selectively impart linear movement of the plunger in the interior chamber to dispense fluid through the nozzle, the ratcheting mechanism and the screw mechanism being configured to selectively operate independently of one another.

13. The indeflator of claim 12, wherein the screw mechanism comprises a threaded rod.

14. The indeflator of claim 13, wherein the screw mechanism comprises an engagement member configured to selectively engage the threaded rod to convert rotational motion of the threaded rod to linear motion to thereby impart linear movement of the plunger in the interior chamber of the barrel.

15. The indeflator of claim 14, wherein the screw mechanism comprises an actuator operatively connected to the threaded rod to impart rotational motion of the threaded rod.

16. The indeflator of claim 12, wherein the ratcheting mechanism comprises a ratchet bar having a length and a plurality of teeth spaced apart along its length.

17. The indeflator of claim 16, wherein the ratcheting mechanism comprises a driving pawl biased toward operative engagement with one of the teeth of the ratchet bar.

18. The indeflator of claim 17, wherein the ratcheting mechanism comprises a trigger operatively connected to the driving pawl to selectively advance the driving pawl and impart linear movement of the plunger in the interior chamber of the barrel.

19. The indeflator of claim 16, further comprising a holding pawl configured to sequentially engage the teeth of the ratchet bar as the plunger moves linearly in the interior chamber of the barrel.

* * * * *